(12) United States Patent
Kobayashi et al.

(10) Patent No.: US 8,198,482 B2
(45) Date of Patent: Jun. 12, 2012

(54) METHOD FOR PRODUCING CARBOXYLIC ACID CHLORIDE

(75) Inventors: Takeshi Kobayashi, Fukuoka (JP); Kiyomi Kido, Fukuoka (JP); Akinori Nagatomo, Fukuoka (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 0 days.

(21) Appl. No.: 12/529,307

(22) PCT Filed: Feb. 27, 2008

(86) PCT No.: PCT/JP2008/053422
§ 371 (c)(1),
(2), (4) Date: Aug. 31, 2009

(87) PCT Pub. No.: WO2008/105464
PCT Pub. Date: Sep. 4, 2008

(65) Prior Publication Data
US 2010/0099911 A1    Apr. 22, 2010

(30) Foreign Application Priority Data
Mar. 1, 2007   (JP) ................................ 2007-051879

(51) Int. Cl.
*C07C 51/58* (2006.01)
(52) U.S. Cl. ....................................... 562/857; 562/861
(58) Field of Classification Search ................... None
See application file for complete search history.

(56) References Cited

U.S. PATENT DOCUMENTS

| | | | | |
|---|---|---|---|---|
| 3,184,506 A | * | 5/1965 | Parker et al. | 562/854 |
| 4,880,576 A | * | 11/1989 | Blank et al. | 562/828 |
| 5,200,560 A | | 4/1993 | Kahl et al. | |
| 5,430,186 A | | 7/1995 | Ksoll et al. | |
| 6,727,384 B1 | | 4/2004 | Busch et al. | |

FOREIGN PATENT DOCUMENTS

| | | |
|---|---|---|
| JP | 56-104837 A | 8/1981 |
| JP | 7-69970 A | 3/1995 |
| JP | 10-130198 A | 5/1998 |
| JP | 2002-363130 A | 12/2002 |
| JP | 2003-509392 A | 3/2003 |
| JP | 2003-509393 A | 3/2003 |
| WO | WO 01/19768 A2 | 3/2001 |

OTHER PUBLICATIONS

International Search Report (PCT/ISA/210) dated Mar. 14, 2008.
Supplementary European Search Report, corresponding to PCT/JP2008/053422, issued on Aug. 3, 2011.
Chinese Office Action issued Mar. 7, 2012, in corresponding Chinese Patent Application No. 200880006819.1, and English translation thereof.

* cited by examiner

*Primary Examiner* — Paul A Zucker
(74) *Attorney, Agent, or Firm* — Buchanan Ingersoll & Rooney PC

(57) ABSTRACT

This invention relates to a method for producing a carboxylic acid chloride, which efficiently decomposes a Vilsmeier reagent type compound in a carboxylic acid chloride lacking a thermal stability or a carboxylic acid chloride hardly distilled in practice due to a high boiling point with a simple operation and has no adverse effect on a subsequent step, and more particularly to a method for producing a carboxylic acid chloride, characterized by comprising reacting a carboxylic acid with a chlorinating agent in the presence of a catalyst, removing the excessive chlorinating agent from a reaction system after the reaction, and then further adding 1.0 to 3.0 equivalents of the starting carboxylic acid based on the catalyst to the reaction system to decompose a Vilsmeier reagent type compound remaining in the reaction system.

3 Claims, No Drawings

METHOD FOR PRODUCING CARBOXYLIC ACID CHLORIDE

TECHNICAL FIELD

This invention relates to a method for producing a carboxylic acid chloride used as a useful intermediate for fine chemicals, medicines, agrichemicals, polyesters and the like, and more particularly to a useful method for producing a carboxylic acid chloride hardly purified through distillation due to its poor thermal stability or hardly distilled in practice due to its high boiling point.

BACKGROUND ART

The carboxylic acid chloride is usually produced through a reaction of a chlorinating agent such as phosgene, oxalyl chloride, phosphorus trichloride, phosphorous pentachloride, thionyl chloride or the like with a carboxylic acid. On this occasion, when an amide type compound is added as a catalyst in order to improve a reaction rate, the chlorinating agent is reacted with the amide type compound to form a Vilsmeier reagent type compound (so-called chloroiminium salt), which serves as active species of a synthesis reaction of an acid chloride. However, when these Vilsmeier reagent type compounds remain, they may often cause a side reaction or a coloring in a subsequent step due to their high activity.

Although depending on a kind of the starting carboxylic acid or a kind of the resulting carboxylic acid chloride, the Vilsmeier reagent type compound is commonly phase-separated to settle out in the form of a brown or black tar at a bottom of a reactor after the completion of the reaction. Therefore, the Vilsmeier reagent type compound is separated through a decantation or the like, and then the carboxylic acid chloride is isolated through distillation-purification. Thus, the carboxylic acid chloride can be easily separated from the Vilsmeier reagent type compound in general, so that there is no problem. Further, even when the Vilsmeier reagent type compound is insufficiently separated, there is known a method comprising polymerizing the Vilsmeier reagent type compound through heat treatment and purifying it by utilizing a boiling point difference or a solubility difference.

However, the resulting carboxylic acid chloride may lack a thermal stability or be hardly distilled in practice due to a high boiling point thereof. Further, the distillation may have to be avoided on an industrial scale, because it overloads a vacuum unit in view of ability and material thereof. In such a case, since the distillation-purification cannot be carried out, the reaction mixture including the dissolved Vilsmeier reagent type compound which cannot be completely separated, i.e., as it is a crude mass, must be used. In that case, there must be a problem such as the side reaction or the coloring due to the Vilsmeier reagent type compound.

Furthermore, some starting carboxylic acids have a high melting point depending on their type and can be often reacted only in the presence of a solvent, and the above-mentioned phase separation of the Vilsmeier reagent type compound is seldom observed. Therefore, the Vilsmeier reagent type compound is compulsorily phase-separated by properly adding a poor solvent such as hexane or the like, or a mixture including all of the Vilsmeier reagent type compound must be used without the distillation.

When the solvent such as hexane or the like is used, it is required to be used in about twice the amount of the carboxylic acid chloride and makes a volumetric efficiency deteriorated, and further the separation and recovery of the solvent make the cost higher. On the other hand, when there is no problem with equipment for the distillation, the distillation may be carried out while including the Vilsmeier reagent type compound, but there is a problem in that a skeleton balance is deteriorated to lower a yield or the like.

As a method for solving the above-mentioned problems, there is known a method using the chlorinating agent in an amount of slightly lower than a theoretical amount based on the carboxylic acid to leave the small amount of the starting carboxylic acid in order not to leave the Vilsmeier reagent type compound. However, it is difficult to precisely adjust the charging amount on the industrial scale, and therefore an equipment cost increases for carrying out. Especially, since phosgene industrially used as the chlorinating agent is supplied as a gas, it is more difficult to adjust the charging amount.

Moreover, when the starting material is a dicarboxylic acid, a reaction system is sophisticated. That is, a shortfall of the chlorinating agent is not equal to the remaining amount of the starting carboxylic acid, and an acid anhydride may be formed depending on a kind of the monoacid chloride or the dicarboxylic acid. Therefore, the method for not leaving the Vilsmeier reagent type compound by adjusting the amount of the chlorinating agent to be charged cannot be carried out.

In addition, there are known a method for improving a hue by contacting with chlorine after or during the reaction (JP-A-2002-363130) and a method for improving a hue by contacting with hydrogen chloride after or during the reaction (JP-A-2003-509393) and thereby the hue is improved, but the Vilsmeier reagent type compound is not removed and therefore the risk of the side reaction cannot be eliminated.

DISCLOSURE OF THE INVENTION

It is, therefore, an object of the invention to provide a method for producing a carboxylic acid chloride, which efficiently decomposes a Vilsmeier reagent type compound in a carboxylic acid chloride lacking a thermal stability or a carboxylic acid chloride hardly distilled in practice due to its high boiling point with a simple operation and has no adverse effect on a subsequent step.

The inventors have made various studies and discovered that after a reaction of a chlorinating agent with a carboxylic acid is completed and then the excessive chlorinating agent is removed, by further adding the starting carboxylic acid, a Vilsmeier reagent type compound is consumed for a reaction to get back to the catalyst, and as a result the invention has been accomplished.

That is, the present invention is a method for producing a carboxylic acid chloride, characterized by comprising:
  reacting a carboxylic acid with a chlorinating agent in the presence of a catalyst;
  removing the excessive chlorinating agent from a reaction system after the reaction; and
  then further adding 1.0 to 3.0 equivalents of the starting carboxylic acid based on the catalyst to the reaction system to decompose a Vilsmeier reagent type compound remaining in the reaction system as a reactive species.

According to the invention, a Vilsmeier reagent type compound as a reactive species remaining in a carboxylic acid chloride lacking a thermal stability or a carboxylic acid chloride having a high boiling point and hardly distilled can be efficiently decomposed with a simple operation, and thereby a carboxylic acid chloride having a high quality and having no adverse effect on a subsequent step can be obtained even not through a distillation-purification step.

BEST MODE FOR CARRYING OUT THE INVENTION

The invention will be described in detail below. As the carboxylic acid used in the invention are mentioned saturated or unsaturated aliphatic carboxylic acids having a carbon number of 16-30 as well as aliphatic dicarboxylic acids (i.e., divalent aliphatic carboxylic acids) and alicyclic dicarboxylic acids having a carbon number of 3-18. Among these carboxylic acids, the aliphatic dicarboxylic acids having a carbon number of 3-12 are preferable in the invention.

As the saturated or unsaturated aliphatic carboxylic acid having a carbon number of 16-30 are mentioned palmitin acid, stearic acid, arachic acid, behenic acid, lignoceric acid, oleic acid, linoleic acid, α-linolenic acid, γ-linolenic acid, arachidonic acid and so on. The carboxylic acid chlorides such as palmitin acid chloride, stearic acid chloride, arachic acid chloride, behenic acid chloride, lignoceric acid chloride, oleic acid chloride, linoleic acid chloride, α-linolenic acid chloride, γ-linolenic acid chloride, arachidonic acid chloride and so on derived from these aliphatic carboxylic acids have a high boiling point and are hardly distilled in practice.

As the dicarboxylic acid having a carbon number of 3-18 are mentioned aliphatic dicarboxylic acids such as malonic acid, succinic acid, fumaric acid, maleic acid, glutaric acid, adipic acid, suberic acid, azelaic acid, sebacic acid, 1,10-decanedicarboxylic acid, 1,12-dodecanedicarboxylic acid, 1,16-hexadecanedicarboxylic acid and so on, and alicyclic dicarboxylic acids such as cyclohexanedicarboxylic acid, cyclohexenedicarboxylic acid and so on. These dicarboxylic acids have a high melting point and can only react in the presence of a solvent, so that the Vilsmeier reagent type compound hardly settles out as a precipitate in the form of a tar and thereby is hardly separated from the resulting dicarboxylic acid dichloride. Further, most of the dicarboxylic acid dichlorides such as aliphatic dicarboxylic acid dichlorides including malonic acid dichloride, succinic acid dichloride, fumaric acid dichloride, maleic acid dichloride, glutaric acid dichloride, adipic acid dichloride, suberic acid dichloride, azelaic acid dichloride, sebacic acid dichloride, 1,10-decanedicarboxylic acid dichloride, 1,12-dodecanedicarboxylic acid dichloride and 1,16-hexadecanedicarboxylic acid dichloride and alicyclic dicarboxylic acid dichlorides including cyclohexanedicarboxylic acid dichloride and cyclohexenedicarboxylic acid dichloride derived from these dicarboxylic acids are poor in a thermal stability and thereby have a problem in that a skeleton balance is deteriorated during the distillation or the like.

As the chlorinating agent used in the invention are mentioned phosgene, oxalyl chloride, phosphorus trichloride, phosphorous pentachloride, thionyl chloride and so on. Among them, phosgene, oxalyl chloride and thionyl chloride are preferably used, since the chlorinating agent itself and a by-product thereof can be easily removed from a reaction system. Further, phosgene is preferably used on an industrial scale.

The amount of the chlorinating agent used in the invention is typically 1.02 to 2.0 equivalents, preferably 1.05 to 1.5 equivalents to a carboxyl group of the carboxylic acid initially charged. When the amount used is less than the range, a reaction does not progress sufficiently. On the other hand, when it is used more than the range, large equipment and much reagent are required to deal with an unreacted chlorinating agent.

The temperature during the reaction of the chlorinating agent with the carboxylic acid is not particularly limited in the invention and depends on a kind of the starting carboxylic acid and a kind of the chlorinating agent, but the reaction is conducted at typically −20° C. to 150° C., preferably 20° C. to 100° C., more preferably 40° C. to 80° C.

In the reaction of the chlorinating agent with the carboxylic acid according to the invention, an organic solvent may be used. When the carboxylic acids have a short carbon chain, they commonly have a low melting point and are liquid at the above-mentioned reaction temperature and therefore a solventless reaction can be carried out. However, the carboxylic acids having a long carbon chain and the dicarboxylic acids are required to react below their melting point, and thereby the organic solvent may be used in order to dissolve or suspend them.

The organic solvent used in the invention for dissolving or suspending the starting carboxylic acid is not particularly limited, as far as it is not substantially reacted with the chlorinating agent or the Vilsmeier reagent type compound, and includes aromatic hydrocarbons such as benzene, toluene, xylene and mesitylene, halogenated hydrocarbons such as methylene chloride, dichloroethane, chloroform, carbon tetrachloride, monochlorobenzene and o-dichlorobenzene, ethers such as tetrahydrofuran and dioxane, and nitriles such as acetonitrile.

The catalyst used in the invention for reacting the chlorinating agent with the carboxylic acid is not particularly limited, as far as it can react with the chlorinating agent to form the Vilsmeier reagent type compound, and includes amide type compounds such as N,N-dimethylformamide (DMF), dimethylacetamide (DMAc) and N-methylpyrrolidone (NMP), and urea type compounds such as 1,3-dimethyl imidazolidinone (DMI), tetramethylurea, tetraethylurea and tetrabutylurea. Among them, DMF, tetramethylurea and DMI are preferable, and DMF is particularly preferable from a viewpoint of availability, cost and reactivity of the corresponding Vilsmeier reagent type compound.

The amount of the catalyst used in the invention is not particularly limited and depends on the kind of the chlorinating agent and the kind of the carboxylic acid, but the catalyst is used within a range of typically 0.1 mol % to 10 mol %, preferably 0.5 mol % to 5 mol %, more preferably 1 mol % to 3 mol % based on the carboxyl group of the carboxylic acid. When the amount used is less than the range, a reaction rate is low and thereby it is usually necessary to conduct the reaction for a long time. While when it is used more than the range, the reaction may not be controlled due to an abnormal rise of the reaction temperature or the like. Further, even if it is used more than the range, the improvement in the reaction rate may not be observed.

In the production method according to the invention, a manner for charging the chlorinating agent and the carboxylic acid is not particularly limited, and includes a method comprising charging the chlorinating agent and the carboxylic acid in the presence or absence of the solvent and then charging the catalyst simultaneously or stepwisely to initiate the reaction, and a method comprising charging the carboxylic acid and the catalyst in the presence or absence of the solvent and then charging the chlorinating agent simultaneously or stepwisely to initiate the reaction. When phosgene (gas) is used as the chlorinating agent, the carboxylic acid and the catalyst are charged in the presence or absence of the solvent and heated to the predetermined reaction temperature, and then the reaction is conducted with injecting the phosgene gas. The injecting period of the phosgene gas depends on the reaction temperature and the amount of the catalyst, but the phosgene gas is preferable to be injected over about 2 hours to 20 hours. When the injecting rate is higher than the range, the phosgene only exiting from the reaction system by a shortcut without reacting increases and the efficiency is deteriorated. On the other hand, when the injecting rate is lower than the range, it is necessary to conduct the reaction for a long time and the production efficiency is deteriorated.

In the production method according to the invention, the excessive chlorinating agent, a reaction by-product, and the Vilsmeier reagent type compound formed from the chlorinating agent and the catalyst exist in the reaction solution after the completion of the reaction. For example, when the phosgene is used as the chlorinating agent, hydrochloric acid and carbon dioxide are referred to as the reaction by-product. These reaction by-product and the excessive chlorinating agent are distilled off from the reaction system at normal pressure or under reduced pressure. Especially when the phosgene is used as the chlorinating agent, the chlorinating agent itself and the reaction by-product are in the form of a gas at normal pressure and therefore can be easily distilled off by injecting a nitrogen gas into a reaction mass. In this case, the solvent used may be simultaneously distilled off, or the Vilsmeier reagent type compound may be decomposed by adding the carboxylic acid while remaining the solvent.

In the production method according to the invention, the decomposition of the Vilsmeier reagent type compound means conversions of the carboxylic acid to the carboxylic acid chloride and of the Vilsmeier reagent type compound to hydrochloric acid and the catalyst by making the carboxylic acid act on the Vilsmeier reagent type compound remaining in the reaction system after the excessive chlorinating agent and the reaction by-product are distilled off from the reaction system. The amount of the carboxylic acid added is 1.0 to 3.0 equivalents, preferably 1.5 to 2.5 equivalents to the catalyst used. When it is less than the range, it does not reach a stoichiometric quantity and the Vilsmeier reagent type compound remains. On the other hand, when it is used more than the range, the added carboxylic acid acts on the target carboxylic acid chloride and thereby an acid anhydride may be produced, or the purity of the target carboxylic acid chloride may be substantially deteriorated due to an equilibrium between the dicarboxylic acid dichloride and the dicarboxylic acid monochloride or the like.

In the production method according to the invention, the temperature during the reaction of the remaining Vilsmeier reagent type compound with the added carboxylic acid is not particularly limited, and may be the temperature during the reaction of the chlorinating agent with the carboxylic acid as the previous step. When the reaction hardly progresses due to a dilute concentration, the temperature may be raised properly.

In the production method according to the invention, the period of the reaction between the remaining Vilsmeier reagent type compound and the added carboxylic acid is not particularly limited, but is typically set to be between 0.5 to 10 hours.

The carboxylic acid chloride thus obtained can be used for various reactions as it is or after the solvent is distilled off. The temperature during the distillation of the solvent is properly set depending on a thermal stability of the resulting carboxylic acid chloride. It is conducted at typically 20° C. to 100° C., preferably 30° C. to 80° C. under normal pressure or reduced pressure.

EXAMPLES

The following examples and comparative examples are given in illustration of the invention in more detail, but the invention is not limited to the examples.

Example 1

292.3 g (2.0 mol) of adipic acid is suspended in 292.3 g of toluene, added with 4.39 g (0.06 mol: 3 mol %/adipic acid) of dimethylformamide (DMF), and then heated to 50° C.-55° C. A reaction is conducted with maintaining the temperature and injecting phosgene gas through a flowmeter at a rate of 45 g/hr. The phosgene gas is injected for about 10 hr in total (total phosgene: 4.4 mol). Then, nitrogen is injected at 48 L/hr for 2 hr at the same temperature to distill off the dissolved phosgene and hydrochloric acid gas. A Vilsmeier reagent type compound floats in a reaction solution, and a part thereof exists at a bottom of a flask in the form of a paste. Then, 5.26 g (0.036 mol: 1.2 equivalents/DMF) of adipic acid is added and agitated for 1 hr. During the agitation, the flotage of the Vilsmeier reagent type compound and the crystal of the adipic acid are completely dissolved. Then, nitrogen is injected at 48 L/hr to distill off hydrochloric acid gas to obtain 645.4 g of a reaction solution. As a result of a GC analysis, a ratio of adipic acid dichloride is 56.7 wt % (2.0 mol) (reaction yield: 98.2%/total adipic acid). Then, the toluene is distilled off at 10 torr and 70° C. in an oil bath. Eventually, an inner temperature reaches 69° C. 371.5 g of a crude adipic acid dichloride is obtained, and as a result of a GC analysis, an adipic acid dichloride content is 97.1 wt %, a toluene content is 1.3 wt %, a DMF content is 0.48 wt %, and an adipic acid monochloride content is 0.43 wt %. A yield of adipic acid dichloride calculated from the purity is 96.8%.

Example 2

236.18 g (2.0 mol) of succinic acid is suspended in 236.2 g of toluene, added with 1.46 g (0.02 mol: 1 mol %/succinic acid) of dimethylformamide (DMF), and then heated to 55° C. A reaction is conducted with maintaining the temperature and injecting phosgene gas through a flowmeter at a rate of 25 g/hr. The phosgene gas is injected for about 16 hr in total (total phosgene: 4.1 mol). Then, nitrogen is injected at 48 L/hr for 2 hr at the same temperature to distill off the dissolved phosgene and hydrochloric acid gas. A Vilsmeier reagent type compound floats in a reaction solution, and a part thereof exists at a bottom of a flask in the form of a paste. Then, 2.60 g (0.022 mol: 2.2 equivalents/DMF) of succinic acid is added and agitated for 1 hr. During the agitation, the flotage of the Vilsmeier reagent type compound and the crystal of the succinic acid are completely dissolved. Then, nitrogen is injected at 48 L/hr to distill off hydrochloric acid gas to obtain 553.5 g of a reaction solution. As a result of a GC analysis, a ratio of succinic acid dichloride is 55.62 wt % (1.99 mol) (reaction yield: 98.2%/total succinic acid). Then, the toluene is distilled off at 20 torr and 70° C. in an oil bath. Eventually, an inner temperature reaches 70° C. 311.4 g of a crude succinic acid dichloride is obtained, and as a result of a GC analysis, a succinic acid dichloride content is 96.4 wt %, a toluene content is 2.1 wt %, a DMF content is 0.51 wt %, and a succinic acid monochloride content is 0.6 wt %. A yield of succinic acid dichloride calculated from the purity is 95.8%.

Example 3

284.5 g (1.0 mol) of stearic acid is suspended in 250.0 g of toluene, added with 2.2 g (0.03 mol: 3 mol %/stearic acid) of dimethylformamide (DMF), and then heated to 50° C. A reaction is conducted with maintaining the temperature and injecting phosgene gas through a flowmeter at a rate of 20 g/hr. The phosgene gas is injected for about 5 hr in total (total phosgene: 1.1 mol). Then, nitrogen is injected at 48 L/hr for 2 hr at the same temperature to distill off the dissolved phosgene and hydrochloric acid gas. A Vilsmeier reagent type compound floats in a reaction solution, and a part thereof exists at a bottom of a flask in the form of a paste. Then, 10.24 g (0.036 mol: 1.2 equivalents/DMF) of stearic acid is added and agitated for 1 hr. During the agitation, the flotage of the Vilsmeier reagent type compound and the crystal of the stearic acid are completely dissolved. Then, nitrogen is injected at 48 L/hr to distill off hydrochloric acid gas to obtain 562.4 g of a reaction solution. As a result of a GC analysis, a ratio of stearic acid chloride is 54.9 wt % (1.02 mol) (reaction yield: 98.5%/total stearic acid). Then, the toluene is distilled off at 10 torr and 70° C. in an oil bath. Eventually, an inner temperature reaches 69° C. 311.2 g of a crude stearic acid chloride is obtained, and as a result of a GC analysis, a stearic acid chloride content is 98.2 wt %, a toluene content is 1.1 wt %, and a DMF content is 0.51 wt %. A yield of stearic acid chloride calculated from the purity is 97.4%.

Comparative Example 1

292.3 g (2.0 mol) of adipic acid is suspended in 292.3 g of toluene, added with 4.39 g (0.06 mol: 3 mol %/adipic acid) of dimethylformamide (DMF), and then heated to 50° C.-55° C. A reaction is conducted with maintaining the temperature and injecting phosgene gas through a flowmeter at a rate of 45 g/hr. The phosgene gas is injected for about 8.3 hr in total (total phosgene: 3.8 mol). Then, nitrogen is injected at 48 L/hr for 2 hr at the same temperature to distill off a small amount of the dissolved phosgene and hydrochloric acid gas. A reaction solution is clear and homogeneous, and an insoluble component is not observed. 603.3 g of a reaction solution is obtained, and as a result of a GC analysis, a ratio of adipic acid chloride is 48 wt % and a reaction yield is 79%/adipic acid. Then, the toluene is distilled off at 10 torr and 70° C. in an oil bath. Eventually, an inner temperature reaches 68° C. 353.7 g of a crude adipic acid dichloride is obtained, and as a result of a GC analysis, an adipic acid dichloride content is 81.0 wt %, a toluene content is 2.0 wt %, a DMF content is 0.48 wt %, and an adipic acid monochloride content is 14.8 wt %. A yield of adipic acid dichloride calculated from the purity is 78.3%/adipic acid.

Comparative Example 2

236.18 g (2.0 mol) of succinic acid is suspended in 236.2 g of toluene, added with 4.39 g (0.06 mol: 3 mol %/succinic acid) of dimethylformamide (DMF), and then heated to 55° C. A reaction is conducted with maintaining the temperature and injecting phosgene gas through a flowmeter at a rate of 33 g/hr. The phosgene gas is injected for about 12 hr in total (total phosgene: 4.1 mol). Then, nitrogen is injected at 48 L/hr for 2 hr at the same temperature to distill off the dissolved phosgene and hydrochloric acid gas. A Vilsmeier reagent type compound floats in a reaction solution, and a part thereof exists at a bottom of a flask in the form of a paste. A GC analysis with respect to 553.5 g of a reaction solution reveals that a ratio of succinic acid dichloride is 55.6 wt % (1.99 mol) (reaction yield: 99.5%/succinic acid). Then, a fractionation under reduced pressure is started at 70° C. and eventually stopped at the time when an inner temperature reaches 100° C. A weight of a toluene fraction is 233.1 g, a weight of an initial fraction is 28.4 g, a weight of an intermediate fraction is 12.2 g, a weight of a main fraction is 248.1 g, and a weight of a residue at the bottom is 34.7 g. A succinic acid dichloride content in the intermediate fraction is 98.8 wt %, and a succinic acid dichloride content in the main fraction is 99.9%. A yield of succinic acid dichloride calculated from a sum of the intermediate fraction and the main fraction is 83.9%/succinic acid.

Comparative Example 3

146.14 g (1.0 mol) of adipic acid is suspended in 146.14 g of toluene, added with 1.46 g (0.02 mol: 2 mol %/adipic acid) of dimethylformamide (DMF), and then heated to 50° C.-55° C. A reaction is conducted with maintaining the temperature and injecting phosgene gas through a flowmeter at a rate of 27 g/hr. The phosgene gas is injected for about 18 hr in total (total phosgene: 4.8 mol). Then, nitrogen is injected at 48 L/hr for 2 hr at the same temperature to distill off the dissolved phosgene and hydrochloric acid gas. A Vilsmeier reagent type compound floats in a reaction solution, and a part thereof exists at a bottom of a flask in the form of a paste. Then, 7.3 g (0.05 mol: 5 equivalents/DMF) of adipic acid is added and agitated for 1 hr. During the agitation, the flotage of the Vilsmeier reagent type compound and the crystal of the adipic acid are completely dissolved. Then, nitrogen is injected at 48 L/hr to distill off hydrochloric acid gas to obtain 321.2 g of a reaction solution. As a result of a GC analysis, a ratio of adipic acid dichloride is 55.7 wt % (0.98 mol) (reaction yield: 93.0%/total adipic acid). Then, the toluene is distilled off at 10 torr and 70° C. in an oil bath. Eventually, an inner temperature reaches 69° C. 192.7 g of a crude adipic acid dichloride is obtained, and as a result of a GC analysis, an adipic acid dichloride content is 90.7 wt %, a toluene content is 2.8 wt %, a DMF content is 0.43 wt %, and an adipic acid monochloride content is 5.1 wt %. A yield of adipic acid dichloride calculated from the purity is 90.9%.

As seen from the Examples 1-3, various carboxylic acid chlorides can be produced by changing a kind of a starting carboxylic acid according to the method of the present invention.

As seen from the Example 1 and the Comparative Example 1, when the amount of phosgene is slightly lower than a theoretical amount thereof in order not to leave the Vilsmeier reagent type compound, the monochloride is produced more than the amount expected from the charging ratio due to an equilibrium of the dichloride and the monochloride.

As seen from the Example 2 and the Comparative Example 2, when the distillation operation is conducted while the Vilsmeier reagent type compound is included, the carboxylic acid chloride obtained as a main fraction has a high quality, but a skeleton balance is deteriorated and a yield falls.

Further, as seen from the Example 1 and the Comparative Example 3, when the carboxylic acid is added more than necessary in order to decompose the Vilsmeier reagent type compound, an amount of the monochloride produced increases to deteriorate the quality, so that the amount of the carboxylic acid to be added after the removal of the excessive chlorinating agent is required to be not more than 3.0 equivalents to the catalyst.

The invention claimed is:

1. A method for producing a carboxylic acid chloride, comprising:
reacting a carboxylic acid with a chlorinating agent in the presence of a catalyst, wherein an amount of the chlorinating agent is 1.02 to 2.0 equivalents to a carboxyl group of the carboxylic acid and the catalyst is at least one selected from the group consisting of N,N-dimethylformamide, tetramethylurea and 1,3-dimethyl imidazolidinone;

removing an excessive chlorinating agent from a reaction system after the reaction; and then further adding 1.0 to 3.0 equivalents of the starting carboxylic acid based on the catalyst to the reaction system to decompose a Vilsmeier reagent type compound remaining in the reaction system.

2. A method for producing a carboxylic acid chloride according to claim 1, wherein the chlorinating agent is phosgene.

3. A method for producing a carboxylic acid chloride according to claim 1, wherein the carboxylic acid is an aliphatic dicarboxylic acid having a carbon number of 3-12.

* * * * *